United States Patent [19]

Kordes

[11] Patent Number: Plant 6,695

[45] Date of Patent: Mar. 28, 1989

[54] ROSE PLANT KORFLAPEI

[75] Inventor: Reimer Kordes, Klein Offenseth, Fed. Rep. of Germany

[73] Assignee: Jackson & Perkins Company, Medford, Oreg.

[21] Appl. No.: 97,583

[22] Filed: Sep. 16, 1987

[51] Int. Cl.[4] ..... A01H 5/00

[52] U.S. Cl. ..... Plt./24

[58] Field of Search ..... Plt./24

*Primary Examiner*—Robert E. Bagwill

*Attorney, Agent, or Firm*—Majestic, Gallagher, Parsons & Siebert

[57] ABSTRACT

A rose variety of the floribunda class is provided having an extremely long vase life for the buds and bright yellow flowers, with the flowers being produced in large quantities and having thick flower petals.

1 Drawing Sheet

SUMMARY OF THE INVENTION

The present invention relates to a new and distinct variety of rose plant of the floribunda class, which was originated by me by crossing an unnamed seedling with the variety Champagne, U.S. Plant Pat. No. 5,411.

The primary objective of this breeding was to produce a new rose variety of the floribunda class bearing flowers with an extremely long vase life, exhibiting a high production of flowers for cutting with a bright yellow color. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Extremely long flower vase life;
2. High flower production;
3. Bright yellow flower color;
4. Extremely small receptacle;
5. Thick petals;
6. Few prickles.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "Korflapei". Color terminology is in accordance with The Royal Horticultural Society Colour Chart except where an ordinary dictionary significance for the color is apparent.

Observations of the buds and flowers were made from specimens grown in a garden at Irvine, Calif. in July.

Flower

This rose plant produces flowers with an extremely long vase life. Cut flowers will last ten to fourteen days under normal vase conditions.

The blooming habit is continuous. The bud size is one to one and one-quarter inches when the petals start to unfurl. The bud form is pointed ovoid. The bud color when sepals first divide is near Yellow Group 12B; when half blown, the upper side of petals is near Yellow Group 12B to 12C fading on the outer petals to White Group 155D, and the lower side of petals is near Yellow Group 12B. The sepals have a color near Green Group 138B. The surface texture is covered with fine hairs. There are three appendaged sepals normally appendaged, and two unappendaged sepals with hairy edge. The receptacle color is near Green Group 138B of a small size, smooth surface and funnel shape. The receptacle is of small size with only a slight funnel shape. The peduncle is of medium length, smooth surface with an occasional gland. Peduncle color is medium green, and the peduncle is stiff, heavy and erect.

Bloom

Bloom size is small to medium, with an average open size of three to three and one-half inches, borne singly or occasionally several together. The stems are strong, and medium to short. The form when first open is high center. This form is retained to the end. All petals curl back quill fashion. Under normal conditions there are thirty-five petals. The upper side of petal is near Yellow Group 12B, as is the reverse side of the petals. The base of petals darkens to Yellow Group 12A with the major color being near Yellow Group 12B. There are no variegations. The general tonality at the end of the first day shows no change in color. At the end of the third day, the outer petals will fade on the plant, but as a cut flower there is little or no fading.

The fragrance is slight. The petal texture is thick, of a round shape and the tips are moderately quilled.

The arrangement is imbricated with no petaloids in the center. The blooms drop off cleanly, and last both on the plant and as a cut flower for a very long time.

Reproductive Parts

There are many anthers of medium size, of yellow color and arranged regularly around the styles. The filaments are yellow, the pollen is gold yellow, the styles are reddish and stigmas are greenish white.

Plant

A very vigorous growth of upright bush form.

Foliage

Medium size, normal in quantity. The new foliage has a slight reddish cast on newest foliage but rapidly becomes green, and the old foliage is dark green. Normal mid-stem leaves have five leaflets.

The leaflets are of an oval pointed shape, are smooth, and have a serrated edge. The serration is single and small in size. Petiole rachis is green and petiole underside is smooth with occasional prickles. Stipules are medium and edged with glands. The foliage is susceptible to mildew under normal growing conditions at Irvine, Calif.

Wood

New wood is green, with a smooth bark. Old wood is green with a smooth bark.

Prickles

There are few prickles on main canes from the base and few on laterals from the main canes. The form is short and straight. Color when young is red.

Parentage

The seed parent was an unnamed seedling; the pollen parent was the variety Champagne, U.S. Plant Pat. No. 5,411.

Classification

Botanical is rosa hybrid. Commercial is floribunda.

I claim:

1. A new and distinct variety of rose plant and parts thereof of the floribunda class substantially as herein shown and described, characterized particularly as to novelty by bright yellow flowers produced substantially continuously in high quantities, cut flowers with a vase life of about ten to fourteen days under normal vase conditions, thick flower petals, few prickles and an extremely small receptacle.

* * * * *

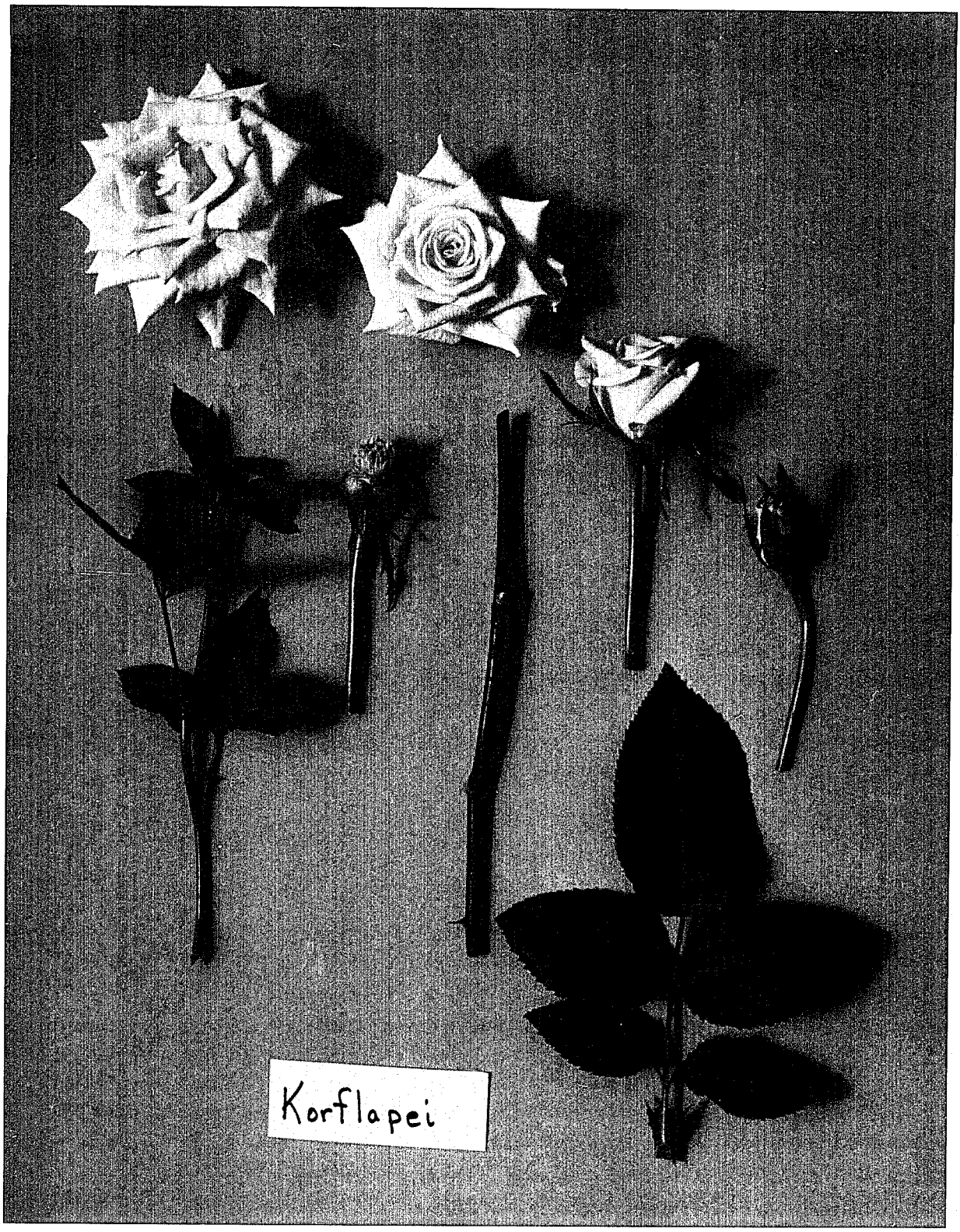
Korflapei